US009302038B2

(12) United States Patent
Stange

(10) Patent No.: US 9,302,038 B2
(45) Date of Patent: Apr. 5, 2016

(54) METHOD AND APPARATUS FOR LIMITING DIAFILTRATE WASTE

(75) Inventor: Katrin Stange, Rostock (DE)

(73) Assignee: Albutec GmbH, Rostock (DE)

(*) Notice: Subject to any disclaimer, the term of this patent is extended or adjusted under 35 U.S.C. 154(b) by 1358 days.

(21) Appl. No.: 12/674,825

(22) PCT Filed: Aug. 19, 2008

(86) PCT No.: PCT/EP2008/060827
§ 371 (c)(1),
(2), (4) Date: Jan. 12, 2011

(87) PCT Pub. No.: WO2009/024566
PCT Pub. Date: Feb. 26, 2009

(65) Prior Publication Data
US 2011/0100909 A1 May 5, 2011

(30) Foreign Application Priority Data
Aug. 23, 2007 (DE) .......................... 10 2007 039 939

(51) Int. Cl.
B01D 65/06 (2006.01)
A61M 1/16 (2006.01)
A61M 1/34 (2006.01)

(52) U.S. Cl.
CPC ........... A61M 1/1696 (2013.01); A61M 1/3431 (2014.02); A61M 1/3437 (2014.02); A61M 1/3468 (2014.02); A61M 1/3472 (2013.01); A61M 1/3486 (2014.02)

(58) Field of Classification Search
USPC ........... 210/636, 321.69, 645, 651, 774, 96.2, 210/130, 259, 266, 321.71, 433.1
See application file for complete search history.

(56) References Cited

U.S. PATENT DOCUMENTS

| 3,579,441 | A | 5/1971 | Brown |
| 4,708,714 | A | 11/1987 | Larsson et al. |
| 5,919,369 | A | 7/1999 | Ash |
| 6,627,151 | B1 | 9/2003 | Borberg et al. |
| 2004/0019312 | A1* | 1/2004 | Childers et al. .............. 604/4.01 |
| 2004/0182783 | A1 | 9/2004 | Walker et al. |

(Continued)

FOREIGN PATENT DOCUMENTS

| DE | 2642535 | 4/1977 |
| DE | 206076 | 1/1984 |

(Continued)

Primary Examiner — Dirk Bass
(74) Attorney, Agent, or Firm — Jordan and Hamburg LLP

(57) ABSTRACT

The present invention describes a process and a device for saving diafiltrate by partial regeneration using adsorbers. An object of the invention is to decrease the requirement of dialysate and/or substitute in the depletion of a substance of class X by means of special microstructured adsorption/filtration devices. An object of the invention is also to enable control of the concentration of a substance group X by hemodialysis and/or hemofiltration, such that by partial recirculation of the diafiltrate in the regeneration circuit, the net throughput of diafiltrate can be kept lower. The process serves for saving dialysate and/or substitute solution in control of the concentration of a substance group X in a complex biological liquid compartment, wherein the net throughput of dialysate and/or substitute is minimized by some of the diafiltrate being regenerated by an internal regeneration cycle (RKL) which is able to deplete substrates or products (substance group Y) of the substance group X in the biological liquid compartment.

39 Claims, 7 Drawing Sheets

(56) References Cited

U.S. PATENT DOCUMENTS

| | | |
|---|---|---|
| 2004/0186410 A1 | 9/2004 | Davidner et al. |
| 2005/0131332 A1* | 6/2005 | Kelly et al. .................. 604/4.01 |
| 2006/0140840 A1* | 6/2006 | Wong ............................ 423/305 |

FOREIGN PATENT DOCUMENTS

| | | |
|---|---|---|
| DE | 3243523 | 5/1984 |
| DE | 3101159 | 8/1985 |
| DE | 4102693 | 9/1993 |
| DE | 4338858 | 4/1995 |
| DE | 19854338 | 6/2000 |
| EP | 0044694 | 1/1982 |
| EP | 0038203 | 7/1985 |
| EP | 0414006 | 2/1991 |
| EP | 1362605 | 11/2003 |
| EP | 1731162 | 12/2006 |
| WO | WO-95/04560 | 2/1995 |
| WO | WO-01/58496 | 8/2001 |
| WO | WO-03/041764 | 5/2003 |
| WO | WO-2005/044339 | 5/2005 |
| WO | WO-2006/002151 | 1/2006 |

* cited by examiner

METHOD AND APPARATUS FOR LIMITING DIAFILTRATE WASTE

FIELD OF THE INVENTION

The present invention describes a method and a device for limiting Diafiltrate waste by partial regeneration using adsorbents.

BACKGROUND OF THE INVENTION

The use of sterile packed hemofiltration substitute solutions represents the largest single cost factor in continuous diafiltration treatment processes. While recent data suggests an improved outcome with higher diafiltrate flow, this might increase process costs.

Specific terms used in the description of the present invention are defined below:

Complex biological fluid compartment (A) is comprised of one or more communicating fluid compartments. Concentrations of chemicals or biochemicals are influenced by formation, distribution, transformation and elimination. Those processes can vary between a biochemical X or Y.

An example of a complex biological fluid compartment are bioreactors with active components, for example liver cells that transform or metabolize toxins. In this case, the reactor medium fluid chamber would be one compartment and the interior of the liver cells a second compartment, both communicating via the cell membrane. Enzymatic processes inside the cell, and transport processes of substances through the cell membrane will affect concentrations of the substances in the reactor medium fluid chamber. Another example of a complex biological fluid compartment (A) is mammal, such as human, blood.

Membrane dialysis/filtration: a combined procedure for monitoring the concentration of substances in a complex biological fluid compartment (A). It is conducted by conducting fluid (A), which is filled with undesired substances along a flow path including a porous membrane which separates (A) from a rinsing side (B) which contains a rinsing fluid and does NOT contain the undesired substances. In the case of dialysis, if the molecular size of the undesired substances are small enough to pass through the pores of the porous membrane then the undesired substances will follow the concentration gradient from (A) to (B), thereby passing to the rinsing side. This process can be supported by a convective transport. In this case, a liquid flow (crossflow) from A to B is applied by a pressure gradient. The substances are then also transported by convection through the membrane, wherein the fluid leaving compartment (A) by filtration (i.e., the filtrate) can be replaced completely or in part by a substitution solution, i.e., substitution fluid (substitute). A combination of dialysis and filtration can occur but in extreme cases can also be applied as only filtration or only dialysis.

Rinsing compartment (B): the compartment that is separated from the complex biological fluid compartment (A) by a separating device, which can be a membrane. rinsing compartment (B) is filled with dialysate, filtrate, or both.

Dialysate is the fluid described above in the definition of "membrane dialysis/filtration", present in in the rinsing compartment (B) and can take up the undesired substances by concentration gradient.

Substitute fluid is the fluid described above in the definition of "membrane dialysis/filtration" which is supplied to compartment (A) as replacement fluid in a filtration process.

Diafiltrate is the fluid described above in the definition of "membrane dialysis/filtration" that is present in the rinsing compartment (B) that has absorbed undesired molecules by diffusion and or convection in the process of cleaning the fluid on the (A) side and is thus enriched with undesired molecules.

Net throughput of dialysate/substitute fluid: the diafiltrate that is removed from the process after a single passage along the membrane filter, thereby not entering the cleaning regeneration cycle (RGC) that is re-supplied to the diafiltrate.

The regeneration cycle (RGC): The regeneration cycle is a device that removes the hereinafter described substance Y out of the diafiltrate, but not the hereinafter described substance X, by means of filtration, adsorption, or biological treatment processes.

Substance group X: one or a plurality of disease-causing substances (undesired molecules), which cannot be eliminated directly by the regeneration cycle (RGC) because known technologies do not provide retention or adsorption capacity for a substance from substance group X. A substance from substance group X can pass the separating device/membrane from (A) to (B) by dialysis or filtration due to pore size and molecular weight range.

Substance X: one or a plurality of substances from substance group X.

Substance group Y: one or a plurality of substances that can be depleted by the regeneration cycle (RGC), because it has retention/adsorption capacity for Y.

Substance Y: one or a plurality of substances from substance group Y.

The cleaning procedure of complex biological fluid compartments systems such as bioreactor fluids or blood by membrane dialysis/filtration today often involves unnecessarily high consumption of dialysate or substitute fluid, as their flow rate needs to be adjusted/increased to the point that the concentration of fast generated undesired toxins can be controlled.

In complex biological fluid compartments, such as in bioreactors for the cultivation of liver cells, this may for example be urea, formed by the Krebs cycle. Urea could be removed from the reactor medium by diafiltration. Also urea accumulates in the bloodstream of patients with kidney damage.

Particularly in the critical care applications of diafiltration, this leads to an often unnecessary consumption of cost intensive sterile prepackaged dialysate and substitute solutions.

Treatment time is adjusted according to the removal of the undesired substance under a given dialysate/filtrate flow. If the removal rate is low due to low flow rates, treatment time must be extended. This may result in prolonged anticoagulation (eg, heparin or citrate), which can have side effects) (e.g., bleeding or alkalosis and hypernatremia).

Extracorporeal blood purification by diafiltration is based on the diffusive (dialysis) and/or convective (diafiltration) transport of permeable molecules from the blood or plasma through a porous membrane into a rinsing solution compartment.

In the case of dialysis and filtration, the rinsing solution should be free of unwanted and undesired substances or toxins. The rinsing solution would be used as a substitute fluid during filtration or as a dialysate in case of dialysis. On the other hand, valuable substances should not be transferred from the biological fluid to the dialysate or filtrate. For example, in the case of blood, glucose is a valuable component that should not be transferred, which can be achieved by maintaining the valuable components at the same concentration in the rinsing solution. In this widely used approach, dialysis fluids are usually mixed from concentrates and reverse osmosis water lines. It needs a complex technology (water treatment systems, dialysis machines). Because of the high technological complexity, trained technicians and dialysis nurses knowledgeable in the logistics of water flow are needed.

Alternative known prior art includes systems with a closed dialysate circuit without continuous flow of dialysate and/or substitute fluid.

In the BioLogic DT system a small closed dialysate reservoir is recycled. The reservoir is regenerated by a suspension of ion exchange resins and a relatively fine-pored charcoal. It is used with no steady dialysate flow which makes for the depletion of dialyzable, but non-absorbed substances. Although the system saves the dialysate, it has not been particularly useful for monitoring the urea and ammonia levels.

In the REDY system, a small closed set dialysate reservoir is regenerated in a recirculation system. The reservoir is regenerated through a complex process that includes charcoal but also requires the decomposition of urea in toxic ammonia by an enzyme (urease) which is secondarily adsorbed chemically by zirconium phosphate.

Because the system saves dialysate due to production of ammonia by the urease it makes an effective removal of ammonia from the patient's blood impossible.

Also, no continuous dialysate flow is used, which would allow the depletion of non adsorbed unwanted substances from blood. It should be noted that many of the undesirable substances in complex biological fluids are not yet known.

In the REDY system, where there is a 100 percent recovery of dialysate or substitute, there is a risk of accumulation of unwanted non-adsorbed substances in the regeneration cycle which compromises the effective cleaning process by dialysis.

In the Genius System, a large volume dialysate reservoir is used. Detoxification utilizes an extremely high volume of dialysate (up to 80 liters). No adsorbents are used. If the concentration is increased in the dialysate to the blood level the system stops working and must be changed.

Combined dialysis and adsorption (e.g. by Renaltech are presented in series and in direct contact with blood, and therefore are less biocompatible and the two mechanisms are not independently adjustable. These adsorbents in direct contact with blood are used to remove non dialyzable substances by adsorption from the blood.

Methods in which adsorbents are used in conjunction with a plasmapheresis filter (plasmapheresis, Prometheus) allow, usually no high trans membrane flows and include risk of loss of important proteins or other valuable materials to the adsorbents.

The MARS procedure (EP 0615780 B1) combines the removal of water-soluble and protein-bound substances. Its uniqueness is that the biological compartment (A), mostly blood, passes through a protein impermeable (blood) side of an asymmetric dialysis membrane, which is coated with proteins that have a bond with toxins with high protein, affinity. On the opposite side of the Dialyzer there is dialysis fluid that contains a dissolved protein with binding capacity for protein bound toxins. Those proteins enter the dialysis membrane fiber which has larger pores on the outside, allowing those proteins entering and diffusing close to the inner side where smaller pores prevent them from entering the blood. This enables passage of albumin bound and small water soluble molecules.

Since these proteins are expensive, the protein-containing dialysate is regenerated by sequential dialysis, followed by serial adsorption by two sorbents. The effect is that albumin bound toxins are finally bound by the sorbents. A differentiated regeneration of the dialysate in the interest of saving the dialysate does not occur. On the contrary, dialysis efficacy is reduced by applying a secondary dialyzer circuit to remove diffusible substances. In published clinical trials (Heemann et al. Hepatology 2002) supporting clinical efficacy, dialysate flow rates of 500 ml/min had been applied in the secondary dialysate circuit.

SUMMARY OF THE INVENTION

An object of the invention is to reduce the net flow (volume/time) of dialysate/substitute rinsing fluids in the depletion of substance X by a regeneration cycle that removes substance Y that are either precursors or metabolites of substance X in the complex biological fluid compartment (A). This is achieved by recycling part of the Diafiltrate via Adsorption-/Filtration (in an RGC). By doing this the net flow rate of the dialysate or filtrate that is flowing into waste bags or drains is minimized, while the concentration of selected markers of substance X in the complex biological fluid compartment does not exceed the targeted values.

The object of the invention is also to possibly control the concentration of substance X by hemodialysis and/or hemofiltration more effectively and aiming at lower concentrations of substance X in the biological system without having to increase the diafiltrate flow. Again, this is done by partial recirculation of used diafiltrate and reduction of substance Y in the regeneration cycle (RGC), so that the net throughput of Diafiltrate remains economically and logistically reasonable.

The present invention describes a method and a device for limiting Diafiltrate waste by partial regeneration using adsorbents.

According to the invention, the object is achieved by the fact that the regeneration cycle (RGC) is based on adsorption and/or filtration properties that remove substance Y from used diafiltrate, reduce the concentration of substance X in complex biological fluid compartments (A) indirectly due to reduced formation or increased metabolism of substance X, even if substance X is not directly removed by the regeneration cycle. This is possible because molecules of substance Y represent either a source/inducer or a metabolite in the degradation of substance X in the framework of metabolic processes in complex biological fluid compartments (A), hence resulting in their reduction in (A).

It was surprisingly observed that urea can be controlled and reduced in such complex biological fluids by partial regeneration of the dialysate through adsorption and/or filtration units to remove metabolites and precursors of urea, but not urea itself.

The advantages of the invention is a better control of concentrations of substance X in complex biological fluid compartments at the lowest possible net loss of sterile dialysate.

The process disclosed herein not only significantly reduces the costs of treatment, but also the logistics of transporting dialysate (typically 4.5 l delivered in heavy bags) will be reduced.

One of the biggest advantages of the invention, however, is the sustainability of intermittent diafiltration treatments. By eliminating substance Y, the reproduction of substance X is delayed or the degradation of substance X is enhanced.

BRIEF DESCRIPTION OF FIGURES

The invention will be explained in more detail through reference to following figures.

DETAILED DESCRIPTION OF THE INVENTION

EXAMPLE 1

Urea as Substance X; Glutamine and/or Ammonia as Substance Y

Figure 1A:
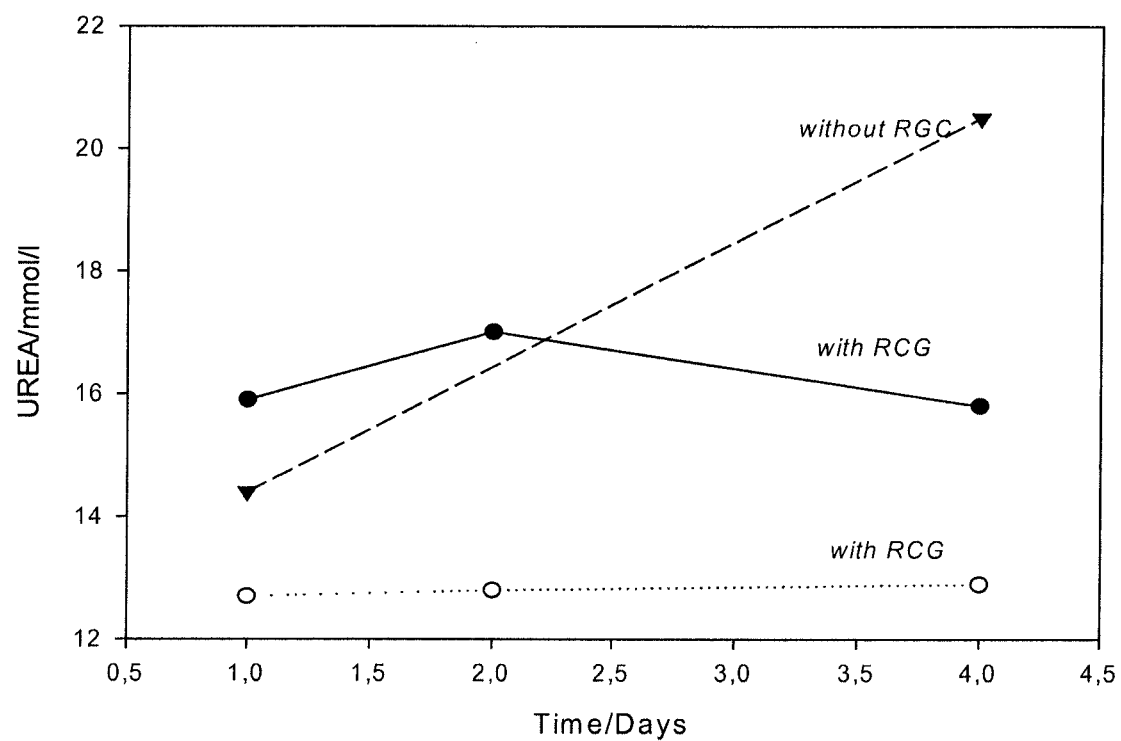
FIG. 1a depicts urea kinetics with and without employing the regeneration cycle shown in the process depicted in FIG.
Figure 3:
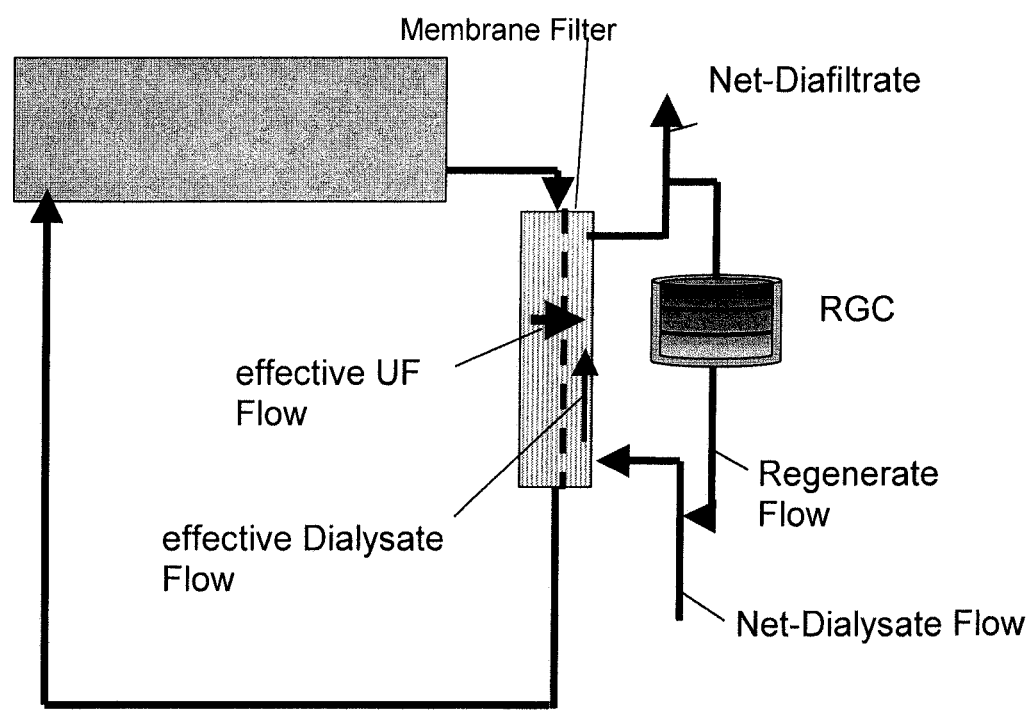
FIG. 3 shows a process diagram of a dialysis process having a regeneration cycle (RGC)

FIG. 3 depicts a flow diagram for a process for carrying out the present invention. The process employs an activated carbon adsorber not having adsorption capacity for urea. A portion of the sterile bicarbonate dialysis fluid (flow 150 ml/min) is recycled during a CVVHD treatment mode with slow blood flow (150 ml/min)), and moderate net diafiltrate flow (50 ml/min)) and thus lower urea clearance (50 ml/min) based on dialyzer blood and dialysis flow. Despite the short treatment time (<8 h) in patients with acute renal failure with a weight of 60 kg, which stands for a Kt/V ratio (clearance times time, divided by body volume) of only 0.48 (which should normally have been maintained above 1) over a treatment period of 3 days, there was an effective reduction of urea with later onset, but continuing after the end of treatment. However, when the same parameters for dialysate flow, blood flow, same dialyzer and treatment time where used in CVVHD not having a regeneration cycle in patients of the same weight and comparable renal dysfunction, a significant increase of the urea concentration was observed (FIG. 1a).

Potential co-variates of urea kinetic, such as endogenous formation by catabolism or renal urea clearance as the cause for this surprising observation were also comparable and could be ruled out.

Figure 1B:
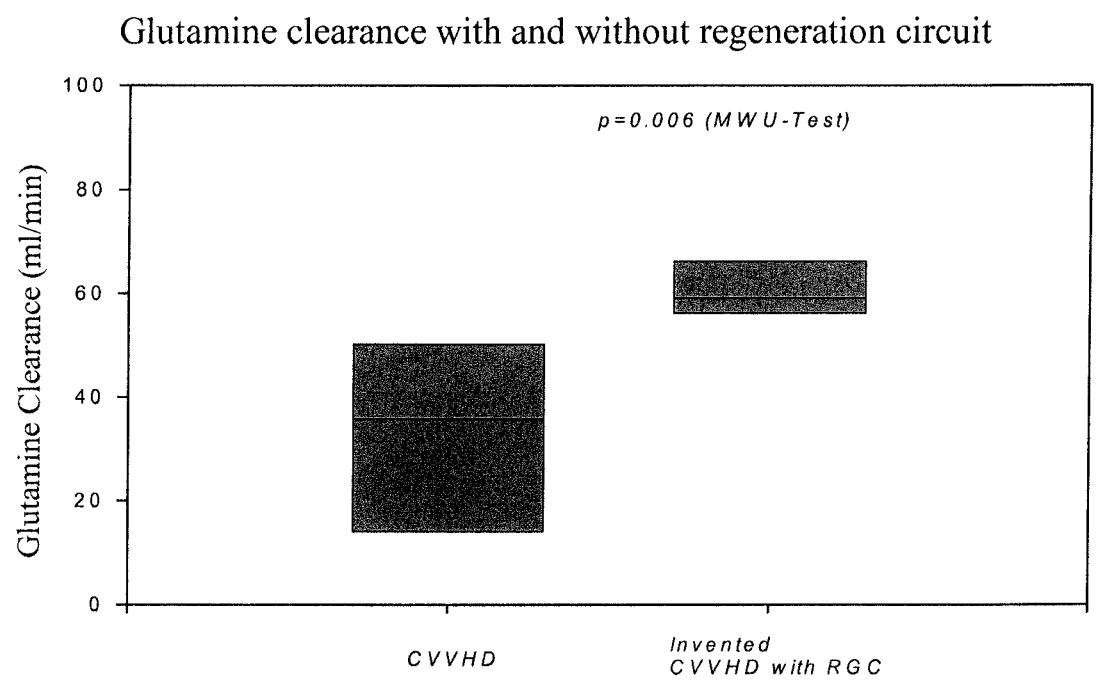
FIG. 1b depicts glutamine clearance at normal CVVHD with and without the regeneration cycle shown in the process depicted in FIG. 3.

In a more detailed investigation of the phenomenon it was found that the internal recycling of the sterile bicarbonate dialysis solution did not lead to direct removal of urea as a target substance, as the activated carbon used in the process has no urea binding capacity. However, it was found that in the partial recycling mode, the glutamine clearance over the dialyzer was significantly higher, indicating glutamine adsorption (FIG. 1b) for the process employing the regeneration circuit as opposed to conventional CVVHD, although in both cases the net flow rate of bicarbonate-based diafiltrate was identical.

In more extensive studies it was shown that good binding capacity for glutamine was enhanced by a microstructure design that targets control of perfusion channels of a charcoal stationary bed adsorbent between 10 nanometers to 100 micrometers. This resulted in complete removal (100%) of glutamine in a single passage which maximized the concentration gradient for glutamine over the membrane despite low net flow of dialysate. In contrast to such stationary bed adsorbent concepts, in the BioLogic DT System adsorbent is arranged as "fluid bed" adsorbents in the dialysate, leading to a significant increase in the diffusion distances between the individual adsorbent particles. Therefore, in BioLogic DT the glutamine clearance is significantly limited due to a higher concentration gradient for glutamine across the membrane. In the present invention though, a partial recycling of diafiltrate using a regeneration circuit based on charcoal with 10 nm to 100 micrometers leads to an effective removal of nitrogen sources which will result in an additional reduction of urea formation.

A special adsorbent can be used either in addition to or in combination with a charcoal filter to remove ammonia, which is a source of nitrogen and thus facilitates control of the urea concentration in complex biological systems.

EXAMPLE 2

Ammonia as Substance X; Glutamine as Substance Y

According to the state of the art, ammonia is effectively removed from complex biological compartments by dialysis when it is set at minimum flow of about 200 ml/min and a dialysate flow of over 500 ml/min at a membrane surface area of 1.3 m (Cordoba et al. 1996).

It has been shown that by using an internal regeneration cycle (RCG) based on activated carbon, an effective decrease of the ammonia occurs, even at considerably lower net flow rate of the dialysate, below 500 ml/min from complex biological systems, which is based on a selective elimination of glutamine related to glutamate concentrations. This again can increase the glutamate/glutamine ratio which is a therapeutic goal.

This was carried out in an in vitro set up completing the following experiments:

Following the model described by Cordoba for building complex biological fluid compartments, a patient model was established by treating each with one liter of plasma in experiments A, B and C and one liter of 5% human albumin solution in experiment D with an initial level of 53 mg of ammonia. The redistribution from the tissue was simulated, by continuous infusion of a solution with 1350 mg/l of ammonia into the patient model. Ammonia concentration in the blood was measured at a rate of 90 ml/min. Experiment D was performed with albumin as a patient model in order to demonstrate that the absence of enzymes in albumin that are present in plasma in trace amounts (eg gamma-glutamyl transferasis-GGT) could provide different kinetics for processing ammonia in the patient undergoing treatment.

In experiment B the patient model was dialyzed with a 1.7 sq. ft. standard dialyzer (patient side flow rate 250 ml/min, net dialysis flow 50 ml min). In experiment C, under otherwise identical conditions, a regeneration cycle having a charcoal filter at 250 ml/min was incorporated. Experiment A was conducted without active detoxification (primary dialysate not activated) in order to document the natural accumulation of toxins in the patient's medium, if no detoxification were to occur. The concentration profile of ammonia in the patient model in A, B, C and D was determined at the beginning and after 10, 20, 30, 45, 60, 90 and 120 minutes. In addition, over the same period, ammonia samples were taken before and after the dialyzer in order to detect ammonia clearance according to the formula:

Clearance=(Patient)blood flow×((Inlet concentration minus outlet concentration)/inlet concentration).

Figure 2:
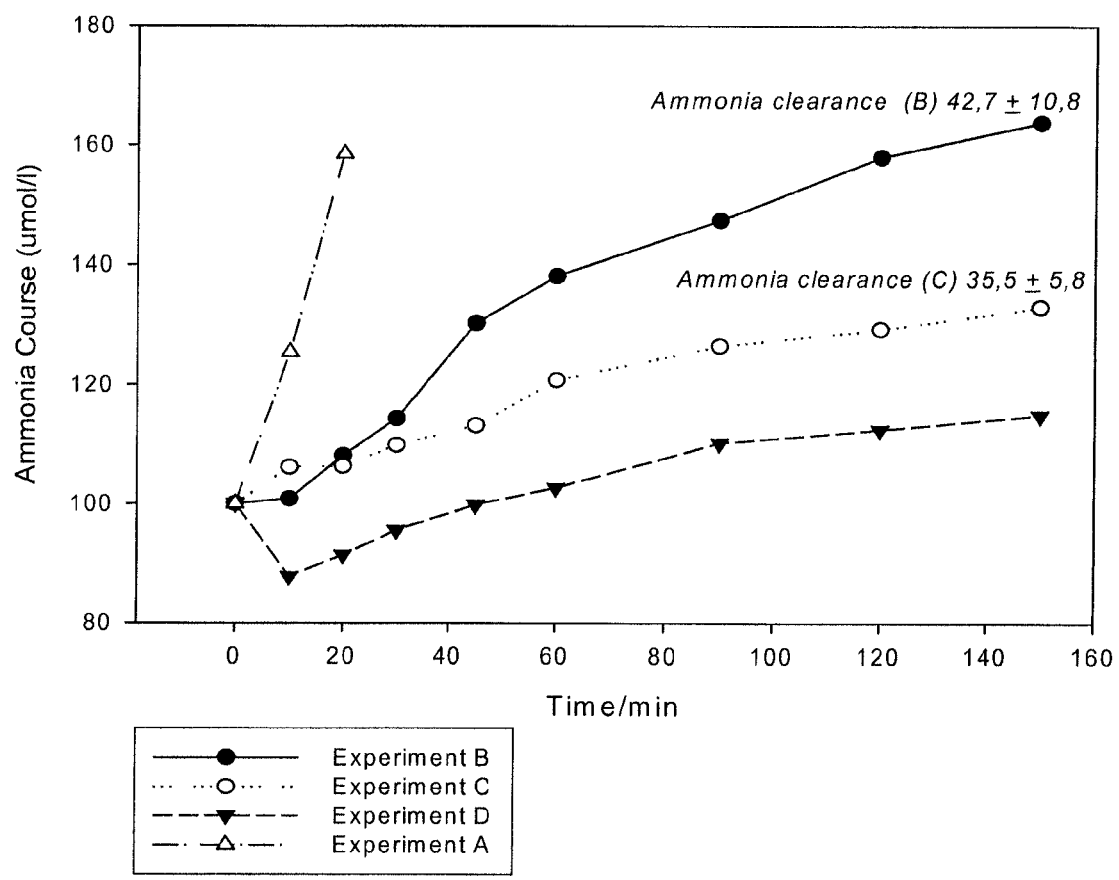
FIG. 2 shows the course of ammonia, in µmol/l, over time (i.e., concentration of ammonia over time, in plasma as a complex biological fluid compartment during standard dialysis with and without the regeneration cycle depicted in FIG. 3.

Concentration changes of ammonia in the patients accounted for the metabolizing of glutamine, ammonia, and ammonia clearance. In addition, ammonia was measured in experiment C before and after the charcoal filter. Patient concentrations of ammonia over time are shown in FIG. 2 for experiments A through D. Compared to a normal dialysis process (represented by B) the presence of a charcoal filter as a RGC can significantly stop ammonia increase (p=0.036, paired Wilcoxon test), as shown in experiment C. However, by detecting the clearance data over the dialyzer it becomes evident that this was not related to dialyzer ammonia clearance, since even though the clearance was not higher, the ammonia reduction was even better (lower increase profile). In addition the ammonia increase in the dialysis model of albumin solutions D was moderate compared to B.

The ammonia tests of experiments B, C and D are shown in FIG. 2. The ammonia increase in control experiment A is only shown over 30 minutes due to axis limit.

The tests demonstrate that plasma as a complex biological fluid is influenced by active biochemistry induced by ammonia (substance X) generation e.g. due to gamma glutamyl transferase activity and that can be prevented by substrate reduction (Glutamine, a substance Y in this case).

EXAMPLE 3

Substance X: Nitric Oxide: Substance Y: Arginine

Nitric oxide is a short-lived radical which is not considered to be removable by extracorporeal therapies.

Including a regeneration circuit (RCG) according to the invention in a CVVHD device which allows improved depletion of arginine by microstructured adsorbents enables control of plasmatic NO levels in plasma.

A CVVHD therapy device with an effective blood flow of 120 ml/min and a dialysate flow of 40 ml/min was equipped according to the invention with a regeneration circuit (RGC) of 100 ml/min with a microstructured charcoal adsorbent (perfusion channel with at maximum 100 μm). For control, a comparable CVVHD was done without RGC.

With RGC included, the nitrate/nitrite level as an indicator for NO in plasma was decreased from 112 to 26 μmol/l within 24 hours, and from 108 to 24 μmol/l in 16 h. With standard CVVH, the NO level increased from 24 to 125 μmol/l within 48 hours. While the dialysis of NO itself is not measurable, Arginine clearance in the regeneration circuit is 72+25 ml/min while standard CVVHD delivers 36+3 ml/min (p<0.05).

EXAMPLE 4

Substance X TNF alpha; Substance Y: IL1

During CVVHF the course of TNF alpha and IL 1 beta was compared between a device that provided a RGC and an otherwise identical device that did not. Blood flow was 150 ml/min, and substitute/filtrate flow during CVVHF was 2.5 l/hour. A highly permeable F50 (Fresenius) filter was used. The regenerated flow in the RGC device was 150 ml/min. All other parameters were identical. IL1 beta and TNF alpha in blood were measured before and after. In addition, the filtration of TNF alpha into the filtrate is measured.

The device having a recirculation mode reached a reduction of TNF alpha in the blood from 150+90 to 100+40 pg/ml (p<0.05 in a paired t-test), whereas standard CVVHF did not result into a significant reduction. Also, the recirculation mode reached a significant reduction of IL1 beta from 9+7 to 6+6 pg/ml (p<0.05 in the paired t-test). The device representing a standard CVVHF process failed to attain a reduction of statistical significance.

Figure 4A:
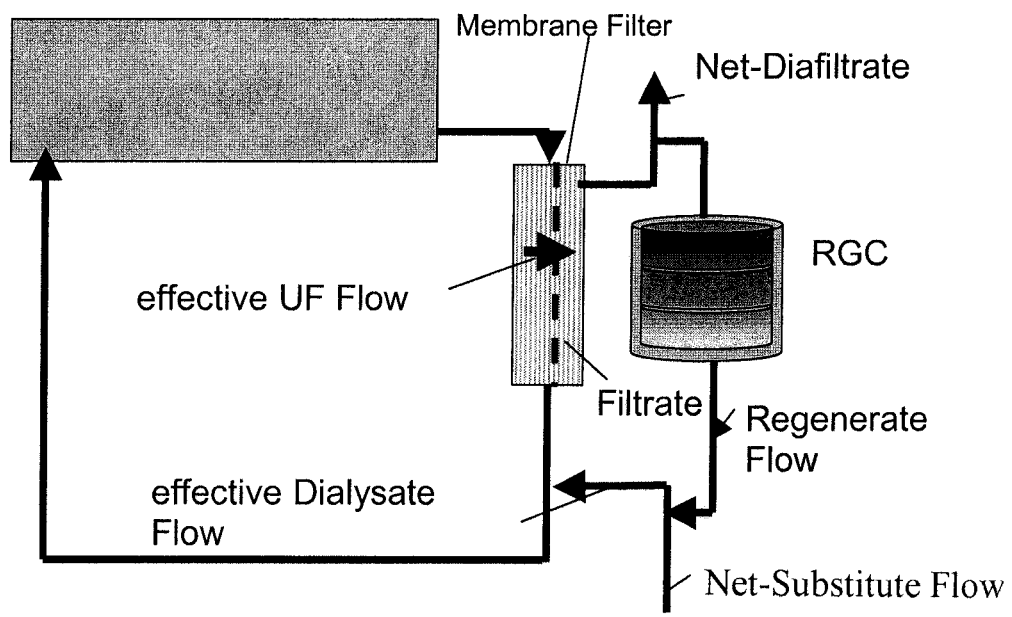
FIGS. 4a and 4b show a circuit diagram for a filtration process where part of the filtrate is recycled in a regeneration cycle (RGC). The substitute flow can either be in the form of "postdilution" i.e. behind the filter (FIG. 4a) or as "predilution" i.e. before the filter (FIG. 4b).
Figure 4B:
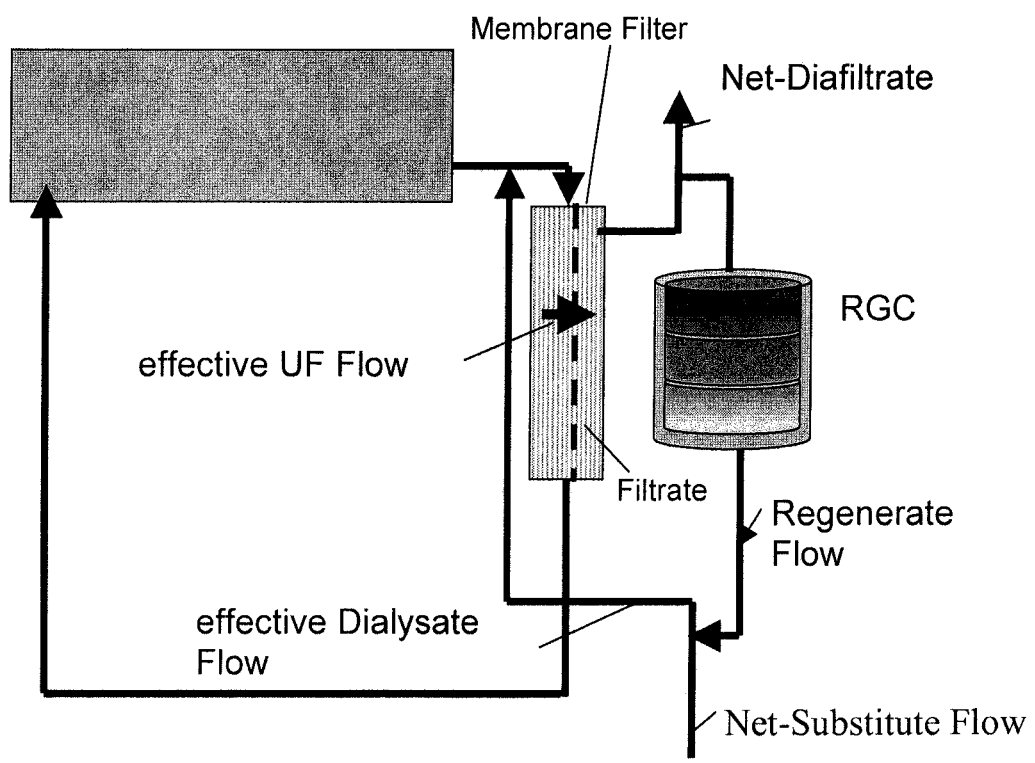
Figure 5:
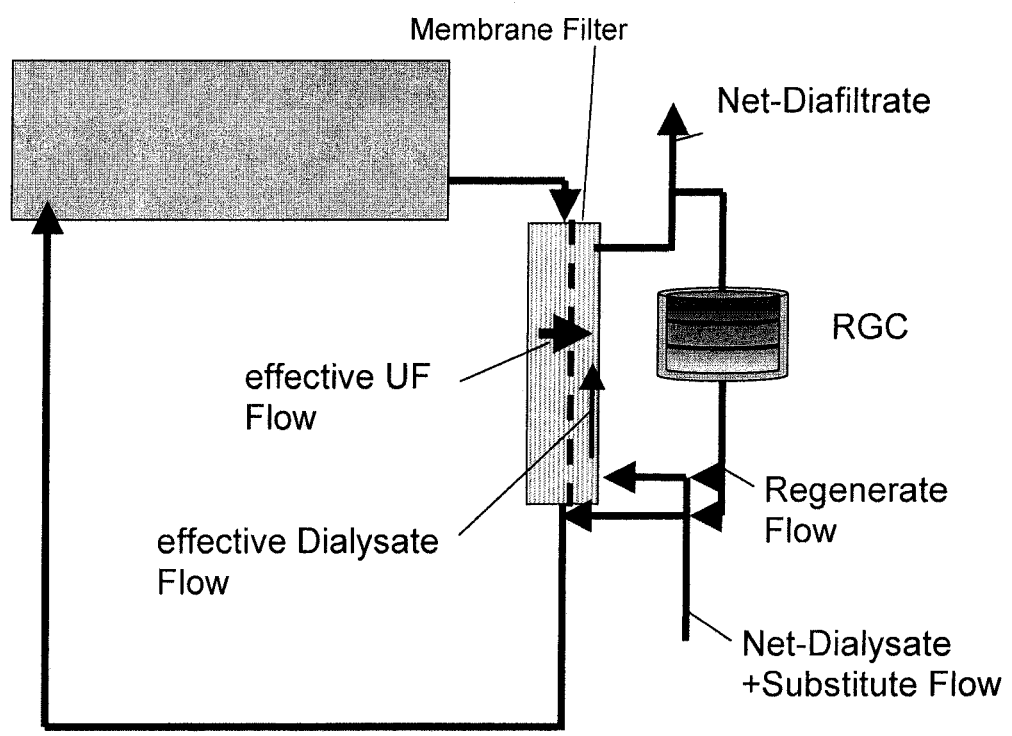
FIG. 5 shows a circuit diagram for a combined dialysis and filtration (diafiltration) with substitution, with both parts of the dialysate as well as the substitute flow comprising filtrate regenerated by regeneration cycle.

FIGS. 3 to 5 depict flow diagrams for alternative processes employed in the present invention, specifically, a dialysis process (FIG. 3), a filtration process (FIGS. 4a and 4b), and a diafiltration process (FIG. 5). FIG. 3 presents a scheme for dialysis having a regeneration circuit. Complex biological fluid compartment A (e.g. blood) is connected via tubes on to an entrance provided on a first side of a separation apparatus provided with a membrane filter. The filter preferably has a pore size in the range between 5,000 Dalton and 500,000 Dalton. Dialysate fluid circulates in the apparatus on a second side of the filter, relative to the first filter side on which the blood flows. Depending on the balancing features of the device, a balanced ultrafiltration is possible (convective by a net stream through the membrane into the dialysate). The diafiltrate splits in two streams after exiting the filter. One stream, the net diafiltrate stream, is discarded as waste and the other stream enters a regeneration circuit (RGC) provided with a substance Y removing component, forming a regenerate stream. With this arrangement, substance Y is retained by the substance Y removing component, but not substance X, and the regenerate stream is replenished with fresh, i.e., net dialysate, which enters the separation apparatus on the second side. The net-diafiltrate stream including substance X is discarded.

FIGS. 4a and 4b depict filtration arrangements in which fluid substitution occurs after dilution of the biological fluid, which occurs in the course of filtration (FIG. 4a), or fluid substitution occurs before dilution (FIG. 4b). A complex biological fluid compartment A (i.e., blood) is connected by tubes to a the first side of a separation apparatus provided with a membrane filter having a pore size in the range set forth above in the description of FIG. 3. Depending on the balancing features of the machine used, a filtrate comprising substance X, substance Y, and a fluid, all of which pass through the membrane from the blood, is generated in the filtrate compartment on a second side of the membrane filter. Depending on the balance desired, replacement fluid (i.e., substitute fluid) is added to biological compartment A either after dilution (i.e., after filtration FIG. 4a) or before dilution (i.e., before filtration FIG. 4b). The filtrate splits in two streams after exiting the filter. One stream, that is the net diafiltrate stream, is discarded and the other stream enters a regeneration circuit (RGC) provided with a substance Y removing component, forming the regenerate stream. With this arrangement, substance Y is retained in the regeneration circuit, but not substance X. Further, the regenerate stream is replenished with net substitute fluid. The net-diafiltrate stream including substance X is discarded.

FIG. 5 depicts a dialysis and filtration (i.e., diafiltration) arrangement employing dialysis fluid and a substitute fluid in which a portion of the regenerated fluid is combined with fresh dialysate fluid and a portion of the regenerated fluid is combined with substitute fluid. A complex biological fluid compartment A (i.e., blood) is connected by tubes to a an apparatus having a membrane filter provided with a pore size in the range set forth above in the description of FIG. 3. The complex biological fluid compartment A flows in the apparatus on one side of the membrane filter. Dialysate fluid circulates on a second side of the membrane filter. Depending on the balancing features of the device, an additional filtration is also possible, with convective stream through the membrane into the diafiltrate compartment. Fluid loss in the biological fluid compartment A is partially or totally replaced with substitute fluid. The diafiltrate is split into two streams after exiting the apparatus. One stream, a/k/a the net diafilatrate steam, is discarded as waste and the other stream enters a regeneration circuit (RGC), forming the regenerate stream. In this arrangement, substance Y is retained in the regeneration circuit by a substance Y removing component present in the regeneration circuit, but not substance X. A portion of the regenerate stream exiting the regeneration circuit is combined with net dialysate, that is, fresh dialysate fluid, which enters the second side of the separation apparatus, and a portion of the regenerate stream is combined with the net substitute fluid, which in turn is combined with the filtered blood at a predetermined location, which could be pre-filtration, post-filtration, or on the blood flow side of the separation apparatus. The net-diafiltrate stream transports substance X as waste. Also, combinations of FIGS. 3 and 4 are possible.

The regeneration circuit includes filters made, but not exclusively, of polysulfone, polyamide, polymethylmethacrylate, polyacrylnitrile. In a procedure to reduce waste of dialysate and or substitution fluids by differenciated control of disease related concentration deviations of metabolites belonging to a group X and Y in a complex biological fluid compartment by membrane dialysis/filtration against or into a cleaning/rinsing solution compartment, in some embodiments the net flow for dialysate and or substitute is less than 500 ml/min. In other embodiments the net flow for dialysate and or substitute is less than 300 ml/min. In other embodiments the net flow for dialysate and/or substitute is less than 100 ml/min. In some embodiments the flow of the internal regeneration circuit is greater than 5 ml/min. In other embodiments, the flow of the internal regeneration circuit is greater than 50 ml/min. In other embodiments, the flow of the internal regeneration circuit is greater than 100 ml/min.

The invention claimed is:

1. A dialysis process for the removal of at least one undesired substance from a biological fluid comprising the steps:
    supplying an unfiltered biological fluid comprising a concentration of a substance X and a concentration of a substance Y that is a precursor or metabolite of the substance X to a first side of a separation apparatus in which the first side is separated from a second side of the separation apparatus by a porous membrane;
    providing a dialysate fluid on the second side of the separation apparatus;
    the porous membrane having pores of a preselected size through which the substance X and the substance Y of the unfiltered biological fluid can pass;
    whereby the substance X and the substance Y pass through the pores to the second side and enter the dialysate fluid, forming a diafiltrate fluid on the second side, the passing of the substance X from the unfiltered biological fluid producing a filtered biological fluid;
    removing the filtered biological fluid from the first side of the separation apparatus;
    removing the diafiltrate fluid from the second side of the separation apparatus;
    separating the diafiltrate fluid into a first fluid and second fluid;
    discarding the first fluid as a net-diafiltrate fluid;
    supplying the second fluid to a regeneration circuit having a substance Y removal component;
    producing a regenerate flow fluid having a reduced concentration of the substance Y by contacting in the regeneration circuit the second fluid with the substance Y removal component, whereby at least a portion of the substance Y is removed from the second fluid, wherein all regeneration in the regeneration circuit occurring during the dialysis process consists of only regeneration of the second fluid by said producing, and that all regeneration of the second fluid occurs without any substance X removal by any of a filtration, an adsorption, or a biological treatment of substance X;
    producing a replenishment dialysate fluid comprised of regenerate flow fluid and fresh dialysate fluid; and
    introducing the replenishment dialysate fluid to the second side of the separation apparatus;
    whereby, the inclusion of the regenerate flow fluid in the replenishment dialysate fluid effects a reduction in a total amount of dialysate fluid employed in the dialysis process;
    wherein regeneration of only a portion of the diafiltrate, by said separating and supplying steps, occurs simultaneously with replacing the discarded diafiltrate with the fresh diasylate fluid by said producing and introducing steps; and
    wherein the substance X is urea, and the substance Y is selected from the group consisting of amino acids, peptides, and proteins, with the proviso that the amino acid is not glutamine, and the substance Y removal component comprises a charcoal-based adsorbent.

2. A filtration process for the removal of at least one undesired substance from a biological fluid comprising:
    supplying an unfiltered biological fluid comprising a concentration of a substance X and a concentration of a substance Y that is a precursor or metabolite of the substance X to a first side of a separation apparatus in which the first side is separated from a second side of the separation apparatus by a porous membrane;
    the porous membrane having pores of a preselected size through which the substance X and the substance Y and a fluid portion of the unfiltered biological fluid can pass;
    whereby the substance X, the substance Y, and the fluid portion of the unfiltered biological fluid pass through the pores to the second side, forming a diafiltrate fluid on the second side of the separation apparatus; whereby the passing of the substance X from the unfiltered biological fluid produces a filtered biological fluid;
    removing the filtered biological fluid from the first side of the separation apparatus;
    removing the diafiltrate fluid from the second side of the separation apparatus;
    separating the diafiltrate fluid into a first fluid and second fluid;
discarding the first fluid as a net-diafiltrate fluid;
    supplying the second fluid to a regeneration circuit having a substance Y removal component;
    producing a regenerate flow fluid having a reduced concentration of the substance Y by contacting in the regeneration circuit the second fluid with the substance Y removal component, whereby at least a portion of the substance Y is removed from the second fluid, wherein all regeneration in the regeneration circuit occurring during the dialysis process consists of only regeneration of the second fluid by said producing, and that all regeneration of the second fluid occurs without any substance X removal by any of a filtration, an adsorption, or a biological treatment of substance X;
    producing a replenishment substitute fluid comprised of the regenerate flow fluid and a substitute fluid;
    combining the replenishment substitute fluid with one of the unfiltered biological fluid, the filtered biological fluid, and a combination of the unfiltered and filtered biological fluid;

whereby, the inclusion of the regenerate flow fluid in the replenishment substitute fluid effects a reduction in a total amount of substitute fluid employed in the filtration process; and wherein regeneration of only a portion of the diafiltrate, by said separating and supplying steps, occurs simultaneously with replacing the discarded diafiltrate with the fresh diasylate fluid by said producing and combining steps.

3. A diafiltration process for the removal of at least one undesired substance from a biological fluid comprising:

supplying an unfiltered biological fluid comprising a concentration of a substance X and a concentration of a substance Y that is a precursor or metabolite of the substance X to a first side of a separation apparatus in which the first side is separated from a second side of the separation apparatus by a porous membrane;

providing a dialysate fluid on the second side of the separation apparatus;

the porous membrane having pores of a preselected size through which the substance X and the substance Y of the unfiltered biological fluid can pass;

whereby the substance X and the substance Y pass through the pores to the second side and enter the dialysate fluid, forming a diafiltrate fluid on the second side, the passing of the substance X from the unfiltered biological fluid producing a filtered biological fluid;

removing the filtered biological fluid from the first side of the separation apparatus;

removing the diafiltrate fluid from the second side of the separation apparatus;

separating the diafiltrate fluid into a first fluid and second fluid;

discarding the first fluid as a net-diafiltrate fluid;

supplying the second fluid to a regeneration circuit having a substance Y removal component;

producing a regenerate flow fluid having a reduced concentration of the substance Y by contacting in the regeneration circuit the second fluid with the substance Y removal component, whereby at least a portion of the substance Y is removed from the second fluid, wherein all regeneration in the regeneration circuit occurring during the dialysis process consists of only regeneration of the second fluid by said producing, and that all regeneration of the second fluid occurs without any substance X removal by any of a filtration, an adsorption, or a biological treatment of substance X;

producing a replenishment dialysate fluid comprised of a first portion of the regenerate flow fluid and fresh dialysate fluid;

producing a replenishment substitute fluid comprised of a second portion of the regenerate flow fluid and a substitute fluid;

introducing the replenishment dialysate fluid to the second side of the separation apparatus;

combining the replenishment substitute fluid with the unfiltered biological fluid;

whereby, the inclusion of the regenerate flow fluid in the replenishment dialysate fluid effects a reduction in a total amount of dialysate fluid employed in the diafiltration process, and the inclusion of the regenerate flow fluid in the replenishment substitute fluid effects a reduction in a total amount of substitute fluid employed in the diafiltration process; and wherein regeneration of only a portion of the diafiltrate, by said separating and supplying steps, occurs simultaneously with replacing the discarded diafiltrate with the fresh diasylate fluid by said introducing and combining steps.

4. The process of claim 3 wherein the substance X is urea, and the substance Y is selected from the group consisting of amino acids, peptides, and proteins, with the proviso that the amino acid is not glutamine, and the substance Y removal component comprises a charcoal-based adsorbent.

5. The process of claim 4 wherein the substance Y removal component further comprises a plurality of channels sized in a range of 10 nanometers to 100 micrometers that provide a short diffusion distance for the substance Y to reach the charcoal-based adsorbent.

6. The process of claim 3 wherein the substance X is urea, the substance Y is ammonia, and the substance Y removal component is free of urease and comprises a zirconium phosphate adsorbent.

7. The process of claim 3 wherein the dialysate fluid comprises a bicarbonate solution.

8. The process of claim 7 wherein the substance Y removal component comprises adsorbents including zirconium phosphate, and the removal of at least a portion of the substance Y from the second fluid occurs at a pH greater than 7.2.

9. The process of claim 3 wherein the substance X is ammonia, the substance Y is glutamine, and the substance Y removal component comprises a charcoal-based adsorbent.

10. The process of claim 3 wherein the substance X is NO, the substance Y is arginine, and the substance Y removal component comprises a charcoal-based adsorbent.

11. The process of claim 3 wherein the substance X is tumor necrosis factor, the substance Y is interleukin 1, and the substance Y removal component comprises a filter having adsorption capacity for interleukin 1.

12. The process of claim 11 wherein the substance Y removal component further comprises a filter made from a material selected from the group consisting of polysulfone, polyamide, polymethylmethacrylate, and polyacrylonitrile.

13. The process of claim 3 wherein the replenishment dialysate fluid has a flow rate less than or equal to 500 ml/min.

14. The process of claim 3 wherein the replenishment dialysate fluid has a flow rate less than or equal to 300 ml/min.

15. The process of claim 3 wherein the replenishment dialysate fluid has a flow rate less than or equal to 100 ml/min.

16. The process of claim 3 wherein the replenishment substitute fluid has a flow rate less than or equal to 500 ml/min.

17. The process of claim 3 wherein the replenishment substitute fluid has a flow rate less than or equal to 300 ml/min.

18. The process of claim 3 wherein the replenishment substitute fluid has a flow rate less than or equal to 100 ml/min.

19. The process of claim 3 wherein the second fluid has a flow rate through the regeneration circuit that is greater than 5 ml/min.

20. The process of claim 3 wherein the second fluid has a flow rate greater than 50 ml/min.

21. The process of claim 3 wherein the second fluid has a flow rate greater than 100 ml/min.

22. The process of claim 3 wherein the porous membrane of the separation apparatus has a pore size in the range of 5,000 to 500,000 Daltons.

23. A process for operating a hemofiltration device to perform dialysis, wherein the hemofiltration device is used to reduce a concentration of a substance group in a complex biological fluid compartment containing an undesired substance group X and substance group Y by way of membrane filtration against or into a rinsing solution compartment, which contains, as a diafiltrate, dialysate and/or substitute solution, the process comprising the following steps:

regenerating only a portion of the diafiltrate in the rinsing solution compartment in a regeneration circuit;

discarding another portion of the diafiltrate as a net flow;

replacing the discarded diafiltrate with fresh dialysate/substitute solution, wherein all regeneration in the regeneration circuit occurring during said dialysis consists of only regeneration of said portion of the diafiltrate to reduce the concentration of substance group Y, and that all regeneration of said portion of the diafiltrate occurs without any substance group X removal by any of a filtration, an adsorption, or a biological treatment of substance group X; and wherein the regenerating step and the discarding and replacing steps take place simultaneously.

24. The process according to claim 23, wherein the net flow is reduced to a minimal volume per time, which maintains the concentration of substance group X in the complex biological fluid compartment in a concentration range desired by the user.

25. The process according to claim 23, wherein the undesired substance group X includes urea, the substance group Y includes glutamine, and the regeneration circuit comprises at least one activated-carbon-based adsorber.

26. The process according to claim 23, wherein the undesired substance group X includes urea, the substance group Y includes amino acids other than glutamine, peptides or proteins, and the regeneration circuit comprises at least one activated-carbon-based adsorber, perfusion channels of which have widths measuring at least 10 nm and at most 100 μm.

27. The process according to claim 23, wherein the undesired substance group X includes urea, the substance group Y includes ammonia, and the regeneration circuit comprises at least one zirconium-phosphate-based adsorber, and excludes urease.

28. The process according to claim 27, wherein the pH value of the filtrate is raised to above 7.2 by a bicarbonate dialysate and/or bicarbonate substitute solution, and subsequently the diafiltrate is conducted over a zirconium-phosphate-containing adsorber at a pH value above 7.2.

29. The process according to claim 23, wherein the undesired substance group X includes ammonia, the substance group Y includes glutamine, and the regeneration circuit comprises at least one activated-carbon-based adsorber.

30. The process according to claim 23, wherein the undesirable substance group X includes nitrogen monoxide, the substance group Y includes arginine, and the regeneration circuit comprises at least one activated-carbon-based adsorber.

31. The process according to claim 23, wherein the undesirable substance group X includes TNF, the substance group Y includes IL1, and the regeneration circuit comprises at least one retention filter with adsorption capacity for IL1.

32. The process according to claim 31, wherein the retention filter with adsorption capacity for IL1 is a semipermeable-membrane-based filter through which a convection flow takes place, and which has a lower nominal molecular weight cut-off than that of the primary membrane filter.

33. The process according to claim 24, wherein the total net flow of dialysate and/or substitute solution is less than 500 ml/min.

34. The process according to claim 25, wherein the flow of the internal regeneration circuit is greater than 5 ml/min.

35. The process according to claim 32, wherein the retention filter comprises: polysulfone, polyamide, polymethyl methacrylate, or polyacrylonitrile.

36. The process according to claim 24, wherein the total net flow of dialysate and/or substitute solution is less than 300 ml/min.

37. The process according to claim 24, wherein the total net flow of dialysate and/or substitute solution is less than 100 ml/min.

38. The process according to claim 25, wherein the flow of the internal regeneration circuit is greater than 50 ml/min.

39. The process according to claim 25, wherein the flow of the internal regeneration circuit is greater than 100 ml/min.

\* \* \* \* \*